(12) United States Patent
Matsumoto et al.

(10) Patent No.: US 9,945,880 B2
(45) Date of Patent: Apr. 17, 2018

(54) AUTOMATIC ANALYZER

(71) Applicant: Toshiba Medical Systems Corporation, Otawara-shi (JP)

(72) Inventors: Satoshi Matsumoto, Nasushiobara (JP); Tetsuya Higashi, Nasushiobara (JP); Masakazu Kitamura, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 3 days.

(21) Appl. No.: 14/322,275

(22) Filed: Jul. 2, 2014

(65) Prior Publication Data
US 2015/0010435 A1    Jan. 8, 2015

(30) Foreign Application Priority Data
Jul. 5, 2013 (JP) ................... 2013-141754

(51) Int. Cl.
*G01N 35/00* (2006.01)
*G01N 35/02* (2006.01)
*G01N 21/25* (2006.01)

(52) U.S. Cl.
CPC ... *G01N 35/0098* (2013.01); *G01N 35/00693* (2013.01); *G01N 35/025* (2013.01); *G01N 21/253* (2013.01); *G01N 2035/00702* (2013.01); *G01N 2201/1242* (2013.01)

(58) Field of Classification Search
CPC ......... G01N 2201/1242; G01N 21/253; G01N 35/0098
See application file for complete search history.

(56) References Cited

U.S. PATENT DOCUMENTS 4,305,723 A * 12/1981 Kolber ................. G01N 21/253
356/246
2012/0252111 A1 * 10/2012 Tono ................. G01N 33/54373
435/288.7

FOREIGN PATENT DOCUMENTS

| JP | S57-030931 A | 2/1982 |
|---|---|---|
| JP | 59-60323 | 4/1984 |
| JP | 61-226661 | 10/1986 |
| JP | 3-146866 | 6/1991 |
| JP | H05-034356 A | 2/1993 |

(Continued)

OTHER PUBLICATIONS

Office Action issued in corresponding Japanese Application No. 2014-120888 dated Dec. 19, 2017.

*Primary Examiner* — P. Kathryn Wright
(74) *Attorney, Agent, or Firm* — Oblon, McClelland, Maier & Neustadt, L.L.P.

(57) ABSTRACT

According to one embodiment, an automatic analyzer includes a magnetic field generator, a photometric unit, a measurement unit, and a decision unit. The magnetic field generator causes magnetic separation in a reaction liquid stored in a cuvette by magnetic particles. The photometric unit includes a light source unit configured to generate light, and a detection unit configured to detect the light generated by the light source unit and generate an output signal corresponding to the detected light. The measurement unit measures a measurement item based on the output signal. The decision unit decides the use range of the output signal to be used to measure the measurement item in accordance with spatial unevenness of the magnetic separation by the magnetic field generator.

18 Claims, 14 Drawing Sheets

(56) References Cited

FOREIGN PATENT DOCUMENTS

| | | | |
|---|---|---|---|
| JP | 07-318559 A | * | 12/1995 |
| JP | 9-80055 | | 3/1997 |
| JP | 2590678 | | 3/1997 |
| JP | 11-326334 | * | 11/1999 |
| JP | 2000-275252 | | 10/2000 |
| JP | 2000-275254 | | 10/2000 |
| JP | 2001-174328 | | 6/2001 |
| JP | 2001-194371 | | 7/2001 |
| JP | 2009-162719 | | 7/2009 |
| JP | 2010-160116 A | | 7/2010 |
| JP | 4598682 | | 12/2010 |
| WO | WO2008142492 | * | 11/2008 |

* cited by examiner

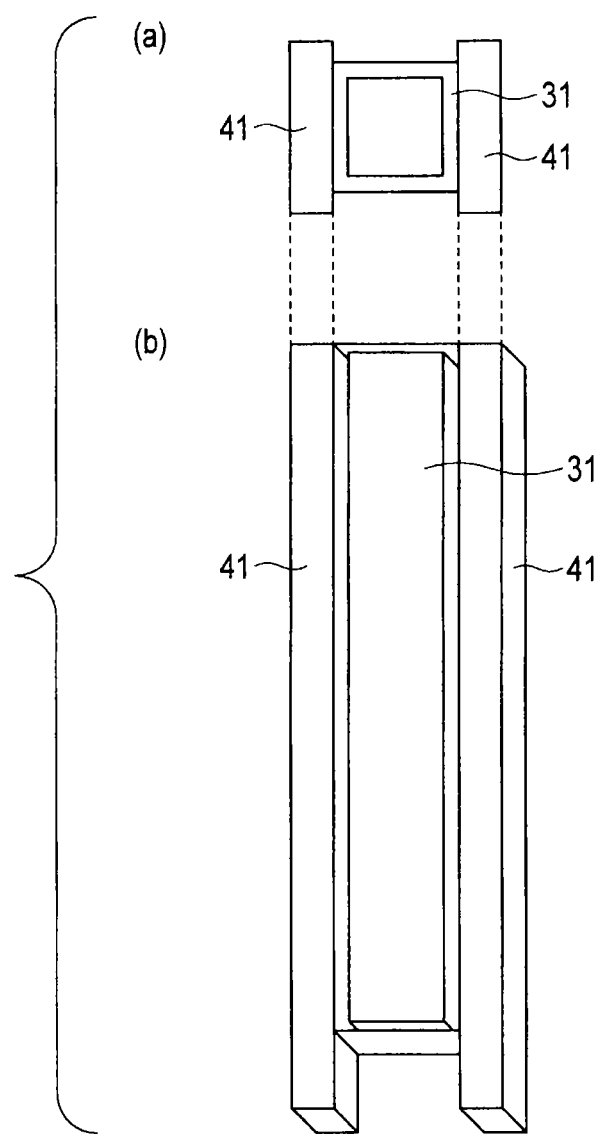
F I G. 3

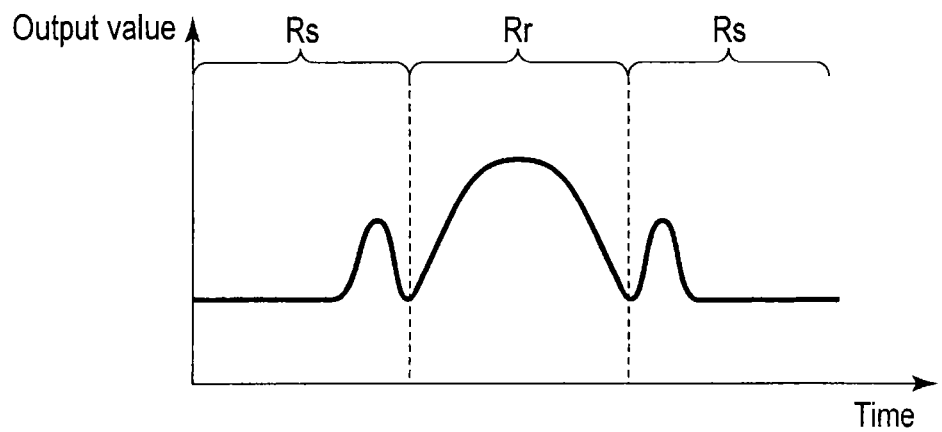
F I G. 6
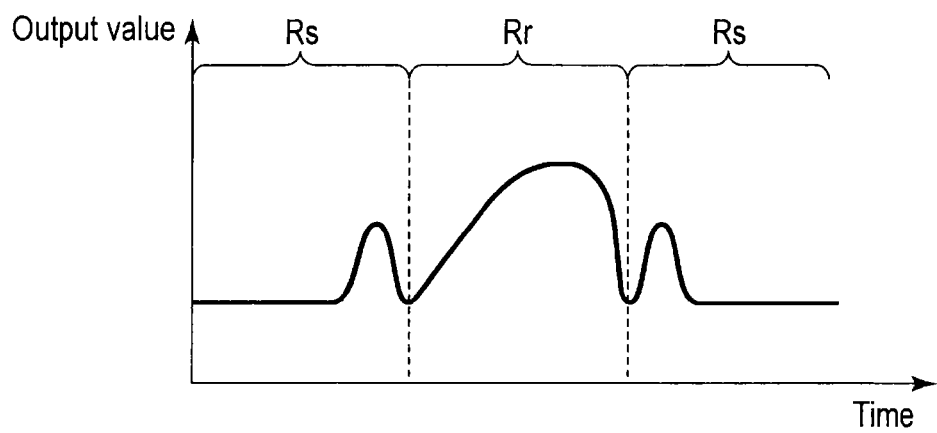
F I G. 7
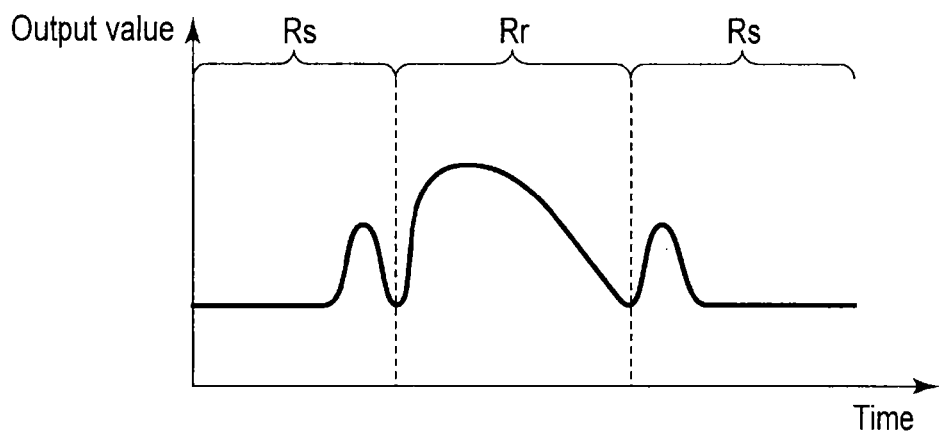
F I G. 8

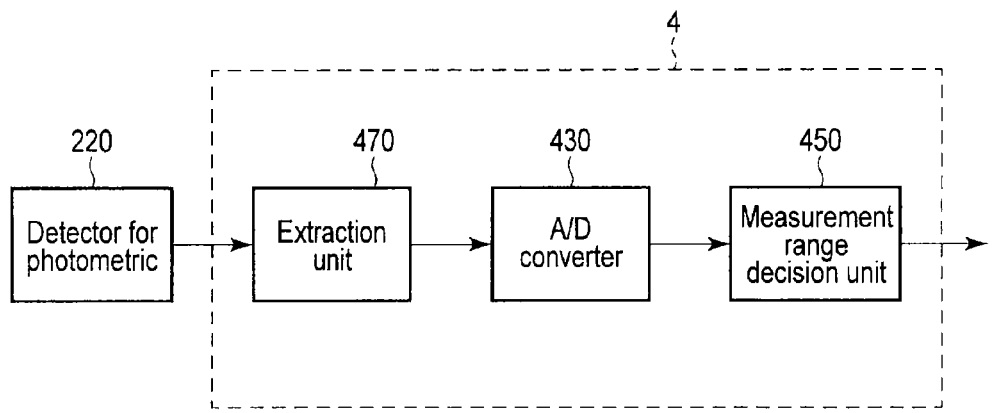
F I G. 9
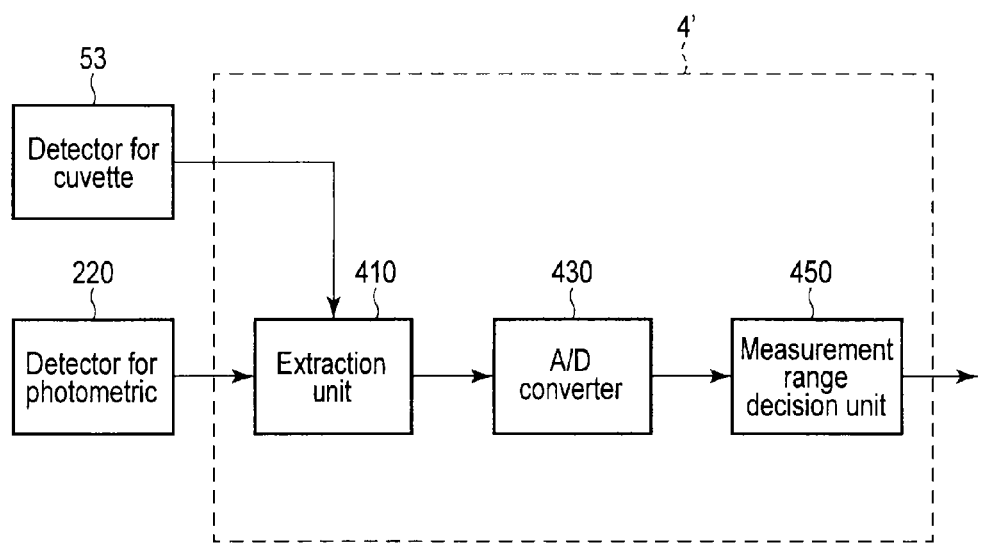
F I G. 10

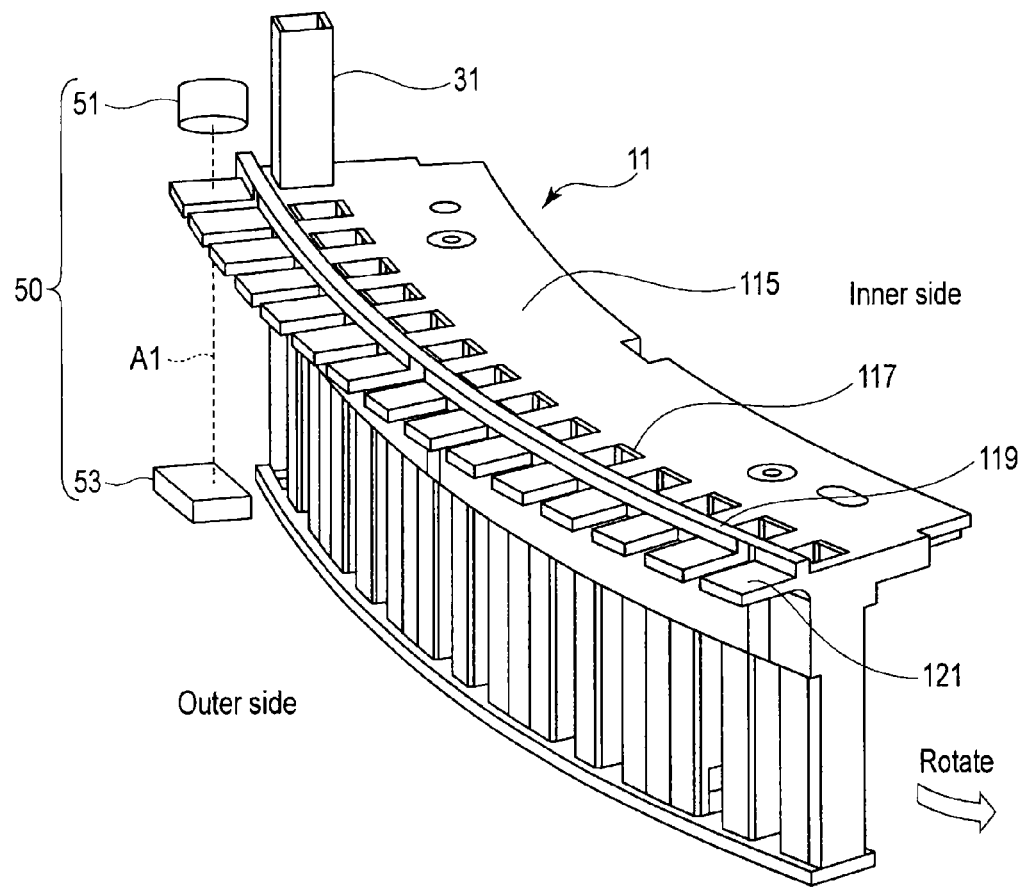
F I G. 11

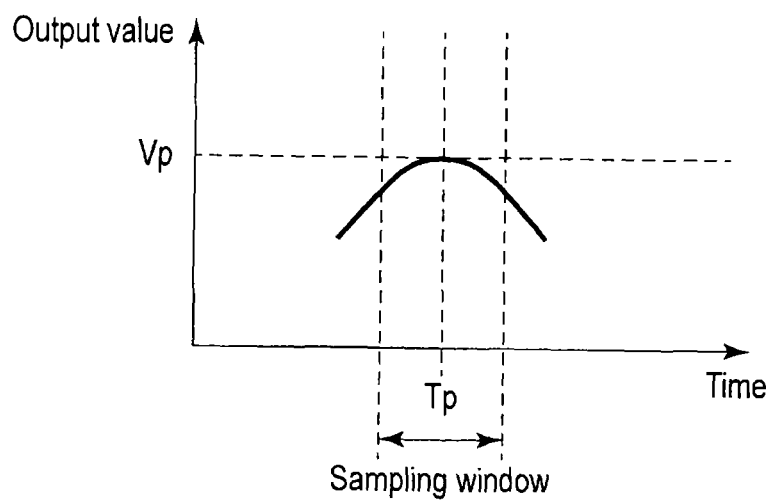
F I G. 13
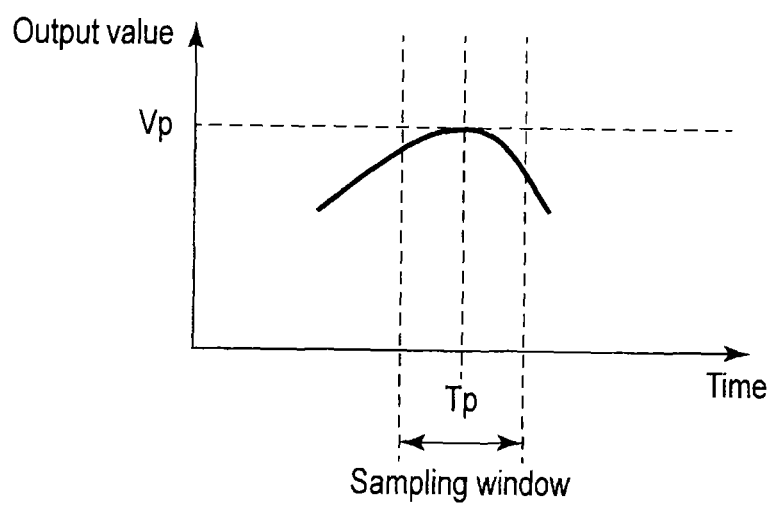
F I G. 14

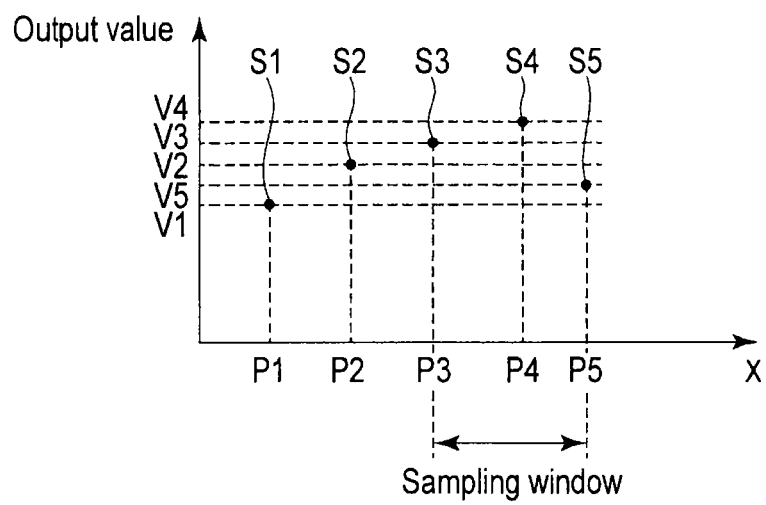
F I G. 19
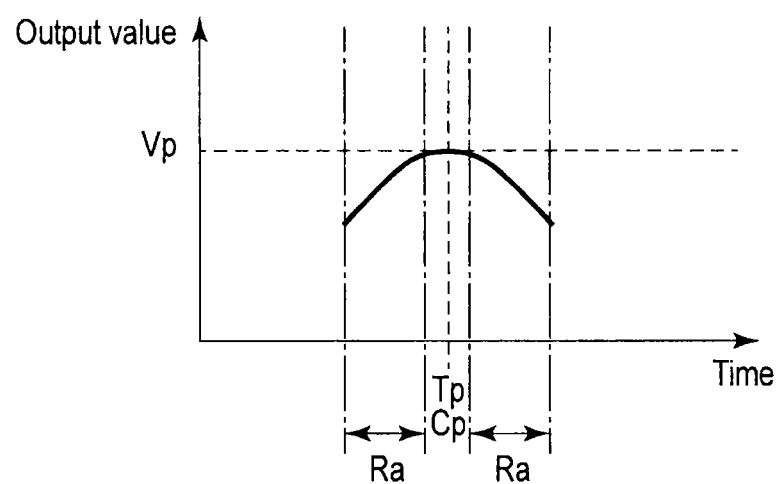
F I G. 20

AUTOMATIC ANALYZER

CROSS-REFERENCE TO RELATED APPLICATIONS

This application is based upon and claims the benefit of priority from the prior Japanese Patent Application No. 2013-141754, filed Jul. 5, 2013 the entire contents of which are incorporated herein by reference.

FIELD

Embodiments described herein relate generally to an automatic analyzer.

BACKGROUND

In an automatic analyzer, a cuvette is repetitively irradiated with light, the light that has passed through the cuvette is repetitively detected, and the measured value of a measurement item is calculated using the average value of detected output values. The sampling window of output values to be used to calculate the average value is set within a predetermined time range.

In recent years, to do inspection by separating detection target molecules using magnetic particles, there has been proposed an automatic analyzer including magnets that apply magnetic fields to a reaction liquid in a cuvette. The magnets are arranged so as to make the flux densities of magnetic fields almost even in the reaction liquid in the cuvette. In some cases, however, magnetic separation does not spatially evenly progress in the cuvette because of rotational motion of a reaction disk, positional shifts of magnets, and the like. The phenomenon that magnetic separation does not spatially evenly progress will be referred to as a fluctuation of magnetic separation hereinafter. When a fluctuation of magnetic separation occurs, the accuracy of a measurement result degrades.

BRIEF DESCRIPTION OF THE DRAWING

FIGS. 3(a) and 3(b) show views schematically illustrating the arrangement of the cuvettes and the magnetic field generators shown in FIG. 2;

FIG. 6 is a timing chart showing the time-varying waveform of a photometric signal according to the embodiment, that is, a typical time-varying waveform in a case where no fluctuation of magnetic separation occurs;

FIG. 7 is a timing chart showing the time-varying waveform of a photometric signal according to the embodiment, that is, an example of a time-varying waveform in a case where a fluctuation of magnetic separation occurs;

FIG. 8 is a timing chart showing the time-varying waveform of a photometric signal according to the embodiment, that is, another example of a time-varying waveform in a case where a fluctuation of magnetic separation occurs;

FIG. 9 is a block diagram showing the arrangement of a signal processing unit according to Example 1 of the embodiment;

FIG. 10 is a block diagram showing the arrangement of the signal processing unit according to Example 2 of the embodiment;

FIG. 11 is a perspective view showing the outer appearance of a cuvette holder and a cuvette detection mechanism in the reaction disk so as to explain the cuvette detection mechanism according to Example 2 of the embodiment;

FIG. 13 is a timing chart showing the time-varying waveform of a photometric signal from an A/D converter in a case where no fluctuation of magnetic separation occurs so as to explain sampling window decision processing by a measurement range decision unit shown in FIG. 10;

FIG. 14 is a timing chart showing the time-varying waveform of a photometric signal from the A/D converter in a case where a fluctuation of magnetic separation occurs so as to explain sampling window decision processing by the measurement range decision unit shown in FIG. 10;

FIG. 19 is another graph showing the output values of the plurality of photometric signals Sn respectively corresponding to the plurality of irradiation regions Pn in a case where a fluctuation of magnetic separation occurs;

FIG. 20 is a timing chart showing the time-varying waveform of a photometric signal from the A/D converter in a case where no fluctuation of magnetic separation occurs so as to explain determination processing of a determination unit shown in FIG. 1;

DETAILED DESCRIPTION

An automatic analyzer according to this embodiment includes a magnetic field generator, a photometric unit, a measurement unit, and a decision unit. The magnetic field generator causes magnetic separation in a reaction liquid stored in a cuvette by magnetic particles. The photometric unit includes a light source unit configured to generate light, and a detection unit configured to detect the light generated by the light source unit and passed through the reaction liquid stored in the cuvette and generate an output signal corresponding to the detected light. The measurement unit measures a measurement item based on the output signal. The decision unit decides the use range of the output signal to be used to measure the measurement item in accordance with spatial unevenness of the magnetic separation by the magnetic field generator.

An automatic analyzer according to this embodiment will now be described with reference to the accompanying drawings.

Figure 1:
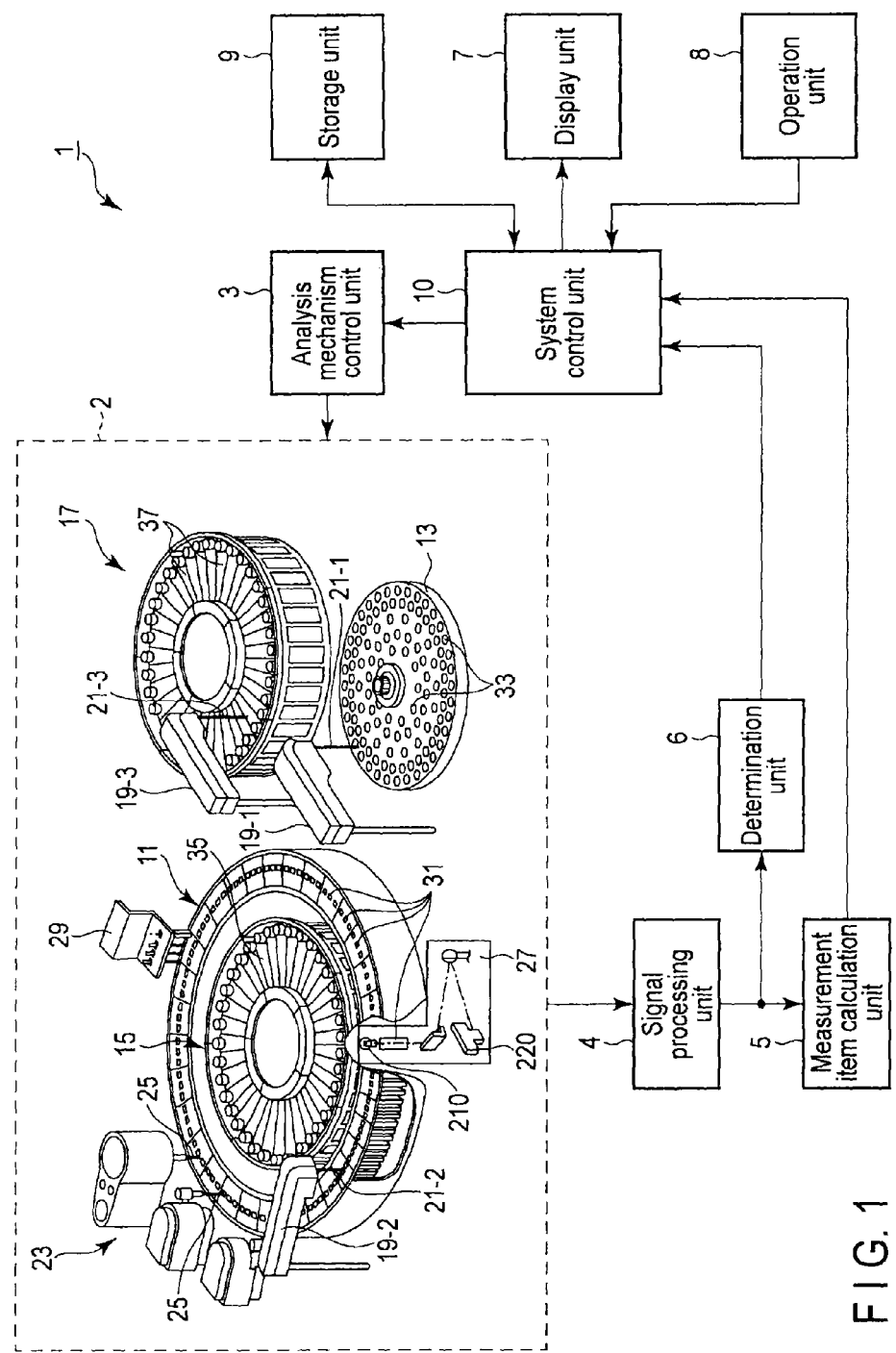
FIG. 1 is a view showing the arrangement of an automatic analyzer according to the embodiment.

FIG. 1 is a view showing the arrangement of an automatic analyzer according to this embodiment. As shown in FIG. 1, an automatic analyzer 1 includes an analysis mechanism 2, an analysis mechanism control unit 3, a signal processing unit 4, a measurement item calculation unit 5, a determination unit 6, a display unit 7, an operation unit 8, a storage unit 9, and a system control unit 10.

The analysis mechanism 2 operates under the control of the analysis mechanism control unit 3. The analysis mechanism 2 is provided in the case of the automatic analyzer. The analysis mechanism 2 includes, for example, a reaction disk 11, a sample disk 13, a first reagent compartment 15, a second reagent compartment 17, a sample arm 19-1, a sample probe 21-1, a first reagent arm 19-2, a first reagent probe 21-2, a second reagent arm 19-3, a second reagent probe 21-3, a stirring arm 23, a stirring blade 25, a photometric mechanism 27, and a cleaning mechanism 29, as shown in FIG. 1.

The reaction disk 11 holds a plurality of cuvettes 31 arranged annularly. The reaction disk 11 alternately repeats rotational motion and stop at a predetermined time interval. As will be described later, the reaction disk 11 is provided with magnetic field generators configured to apply magnetic fields to the cuvettes 31. The cuvettes 31 are formed from, for example, glass. The sample disk 13 is arranged near the reaction disk 11. The sample disk 13 holds sample containers 33 each storing a sample. The sample disk 13 rotates so as to locate the sample container 33 storing a sample to be dispensed at the sample aspirate position. The first reagent compartment 15 holds a plurality of first reagent containers 35 each storing a first reagent that selectively reacts with a sample inspection item. The first reagent compartment 15 rotates so as to locate the first reagent container 35 storing a first reagent to be dispensed at the first reagent aspirate position. The second reagent compartment 17 is arranged near the reaction disk 11. The second reagent compartment 17 holds a plurality of second reagent containers 37 each storing a second reagent corresponding to a first reagent. The second reagent compartment 17 rotates so as to locate the second reagent container 37 storing a second reagent to be dispensed at the second reagent aspirate position.

In this embodiment, a solution containing magnetic particles that directly or indirectly specifically bond to the substance of inspection target molecules included in a sample is used as the first reagent or second reagent. The detection target substance can quantitatively be analyzed at a high sensitivity.

The sample arm 19-1 is arranged between the reaction disk 11 and the sample disk 13. The sample probe 21-1 is attached to the distal end of the sample arm 19-1. The sample arm 19-1 supports the sample probe 21-1 so that it can move in the vertical direction. The sample arm 19-1 also supports the sample probe 21-1 so that it can rotate along an arcuate path. The path of the sample probe 21-1 passes through the sample aspirate position on the sample disk 13 and the sample discharge position on the reaction disk 11. The sample probe 21-1 aspirates the sample from the sample container 33 arranged at the sample aspirate position on the sample disk 13, and discharges the sample into the cuvette 31 arranged at the sample discharge position on the reaction disk 11.

The first reagent arm 19-2 is arranged near the outer periphery of the reaction disk 11. The first reagent probe 21-2 is attached to the distal end of the first reagent arm 19-2. The first reagent arm 19-2 supports the first reagent probe 21-2 so that it can move in the vertical direction. The first reagent arm 19-2 also supports the first reagent probe 21-2 so that it can rotate along an arcuate path. The path of the first reagent probe 21-2 passes through the first reagent aspirate position on the first reagent compartment 15 and the first reagent discharge position on the reaction disk 11. The first reagent probe 21-2 aspirates the first reagent from the first reagent container 35 arranged at the first reagent aspirate position on the first reagent compartment 15, and discharges the first reagent into the cuvette 31 arranged at the first reagent discharge position on the reaction disk 11.

The second reagent arm 19-3 is arranged between the reaction disk 11 and the second reagent compartment 17. The second reagent probe 21-3 is attached to the distal end of the second reagent arm 19-3. The second reagent arm 19-3 supports the second reagent probe 21-3 so that it can move in the vertical direction. The second reagent arm 19-3 also supports the second reagent probe 21-3 so that it can rotate along an arcuate path. The path of the second reagent probe 21-3 passes through the second reagent aspirate position on the second reagent compartment 17 and the second reagent discharge position on the reaction disk 11. The second reagent probe 21-3 aspirates the second reagent from the second reagent container 37 arranged at the second reagent aspirate position on the second reagent compartment 17, and discharges the second reagent into the cuvette 31 arranged at the second reagent discharge position on the reaction disk 11.

The stirring arm 23 is arranged near the outer periphery of the reaction disk 11. The stirring blade 25 is attached to the distal end of the stirring arm 23. The stirring arm 23 supports the stirring blade 25 so that it can move in the vertical direction. The stirring arm 23 also supports the stirring blade 25 so that it can rotate along an arcuate path. The stirring blade 25 stirs the solution mixture of the sample and the first reagent or the solution mixture of the sample, the first reagent, and the second reagent in the cuvette 31 arranged at the stirring position on the reaction disk 11. These solution mixtures will be referred to as reaction liquids hereinafter.

As shown in FIG. 1, the photometric mechanism 27 is provided near the reaction disk 11. The photometric mechanism 27 operates under the control of the analysis mechanism control unit 3. More specifically, the photometric mechanism 27 includes a light source 210 and a detector 220 for photometric. The light source of the photometric mechanism will be referred to as a photometric light source, and the photodetector as a photometric detector hereinafter. The photometric light source 210 emits light to a photometric position in the reaction disk 11. The photometric detector 220 is arranged at a position facing the photometric light source with the photometric position between them. The photometric detector 220 detects the light emitted by the photometric light source and transmitted through the cuvette 31 and the reaction liquid. The photometric detector 220 generates an analog output signal having an output value corresponding to the intensity of the detected light. The output signal from the photometric detector 220 will be referred to as a photometric signal hereinafter. The generated photometric signal is supplied to the signal processing unit 4.

The cleaning mechanism 29 is provided on the outer periphery of the reaction disk 11. The cleaning mechanism 29 operates under the control of the analysis mechanism control unit 3. More specifically, a cleaning nozzle and a dry nozzle are attached to the cleaning mechanism 29. The cleaning mechanism 29 cleans the cuvette 31 located at the cleaning position of the reaction disk 11 by the cleaning nozzle and dries it by the dry nozzle.

The analysis mechanism control unit 3 operates the devices and mechanisms of the analysis mechanism 2 under the control of the system control unit 10. The signal processing unit 4 generates a digital output signal based on the photometric signal from the photometric detector 220. The signal processing unit 4 also decides the use range of a photometric signal to be used to measure a measurement item by the measurement item calculation unit 5 in accordance with the spatial unevenness of magnetic separation by the magnetic field generators. In other words, the signal processing unit 4 corrects the use range in accordance with the spatial unevenness of magnetic separation by the magnetic field generators. More specifically, the signal processing unit 4 decides the time range of a photometric signal to be used to measure a measurement item for each of the plurality of cuvettes in accordance with the time-varying waveform of a photometric signal from the photometric detector 220. The time range of a photometric signal to be used to measure a measurement item will be referred to as a sampling window hereinafter. The measurement item calculation unit 5 calculates the measured value of a measurement item for each of the plurality of cuvettes based on a photometric signal within the sampling window. The determination unit 6 determines for each of the plurality of cuvettes 31 whether an extreme value is included in the time range out of the time-varying waveform of a photometric signal from the signal processing unit 4. The display unit 7 includes a display device such as a CRT display, a liquid crystal display, an organic EL display, or a plasma display. The display unit 7 displays a calculation result of the measurement item calculation unit 5 or a determination result of the determination unit 6. The operation unit 8 receives various kinds of instructions and information input from the operator via an input apparatus. As the input apparatus, a pointing device such as a mouse or track ball, a selection device such as a switch button, or an input device such as a keyboard can appropriately be used. The storage unit 9 stores the operation program of the automatic analyzer 1, and the like. The system control unit 10 functions as the main unit of the automatic analyzer 1. The system control unit 10 reads out the operation program from the storage unit 9, and controls the units in accordance with the operation program.

The automatic analyzer 1 according to this embodiment will be described below in detail.

The arrangement of the cuvettes 31 and magnetic field generators 41 in the reaction disk 11 will be described first with reference to FIG. 2.

Figure 2:
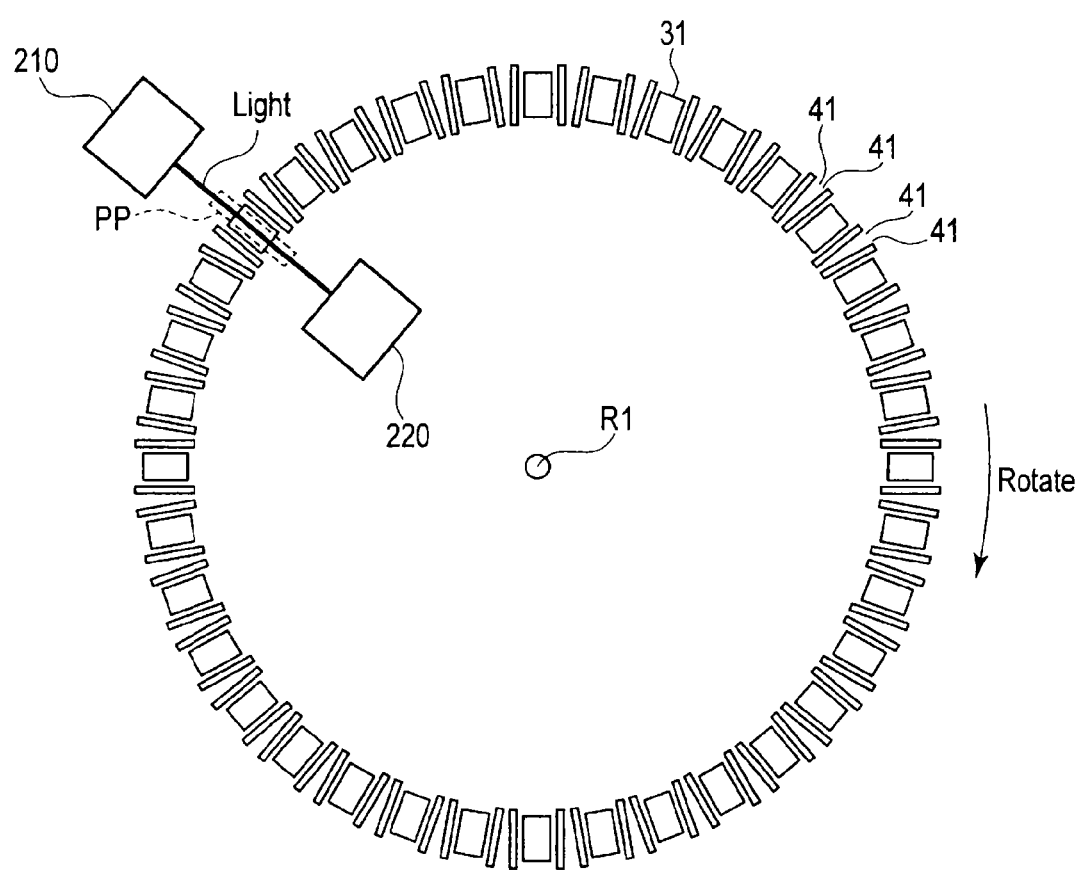
FIG. 2 is a view schematically showing the arrangement of a plurality of cuvettes and a plurality of magnetic field generators in a reaction disk shown in FIG. 1.

FIG. 2 is a view schematically showing the arrangement of the plurality of cuvettes 31 and the plurality of magnetic field generators 41 in the reaction disk 11. FIG. 3 shows views schematically illustrating the arrangement of the cuvette 31 and the magnetic field generators 41. In FIG. 3, (a) is a plan view of the cuvette and the magnetic field generators 41. In FIG. 3, (b) is a perspective view of the cuvette and the magnetic field generators 41.

As shown in FIG. 2, the plurality of cuvettes 31 are arranged in the reaction disk 11 along a circle with respect to a rotating shaft R1 as the center. The plurality of cuvettes 31 are intermittently repetitively rotated and stopped about the rotating shaft R1 by the reaction disk 11. A pair of magnetic field generators 41 are arranged so as to sandwich each cuvette 31. The pair of magnetic field generators 41 are arranged to apply magnetic fields along the rotation direction of the cuvette 31. As the magnetic field generator 41 according to this embodiment, any object capable of generating a magnetic field is applicable. More specifically, a magnet is employed as the magnetic field generator 41. As the magnet 41 according to this embodiment, any existing magnet is applicable. For example, a permanent magnet such as a ferrite magnet, an alnico magnet, a samarium-cobalt magnet, or a neodymium magnet is preferably used as the magnet 41. A combination of a permanent magnet and another magnetic material may be used as the magnet 41. The magnet 41 may contain a ferromagnetic material such as a metal, an alloy, or an oxide. The magnet 41 may include an electromagnet. In this case, the magnet 41 (magnetic circuit) formed from an electromagnet and a permanent magnet or another magnetic material is formed, like the above-described ferromagnetic material. The magnetic field generator 41 is assumed to be a magnet hereinafter. The pair of magnetic field generators 41 are arranged so as to sandwich each cuvette 31, thereby applying magnetic fields to the reaction liquid in the cuvette 31.

As shown in FIG. 2, the photometric mechanism 27 includes the photometric light source 210 and the photometric detector 220. The photometric light source 210 and the photometric detector 220 are fixed at predetermined positions in the case of the automatic analyzer 1. The photometric light source 210 emits light toward the photometric detector 220. A photometric position PP is provided at a predetermined position on the optical path from the photometric light source 210 to the photometric detector 220. The cuvettes 31 are rotated by the reaction disk 11 at a predetermined time interval so as to pass across the light from the photometric light source 210 at the photometric position PP almost at the right angle. The pair of magnets 41 are arranged so as to apply magnetic fields along the passage direction of the cuvette 31 with respect to the photometric position PP. Alternatively, the pair of magnets 41 are arranged so as to face each other in a direction perpendicular to the transmission direction of the light generated by the photometric light source 210. The reaction liquid in the cuvette 31 is optically measured by the photometric mechanism 27 every time the cuvette 31 passes across the photometric position PP.

Figure 4:
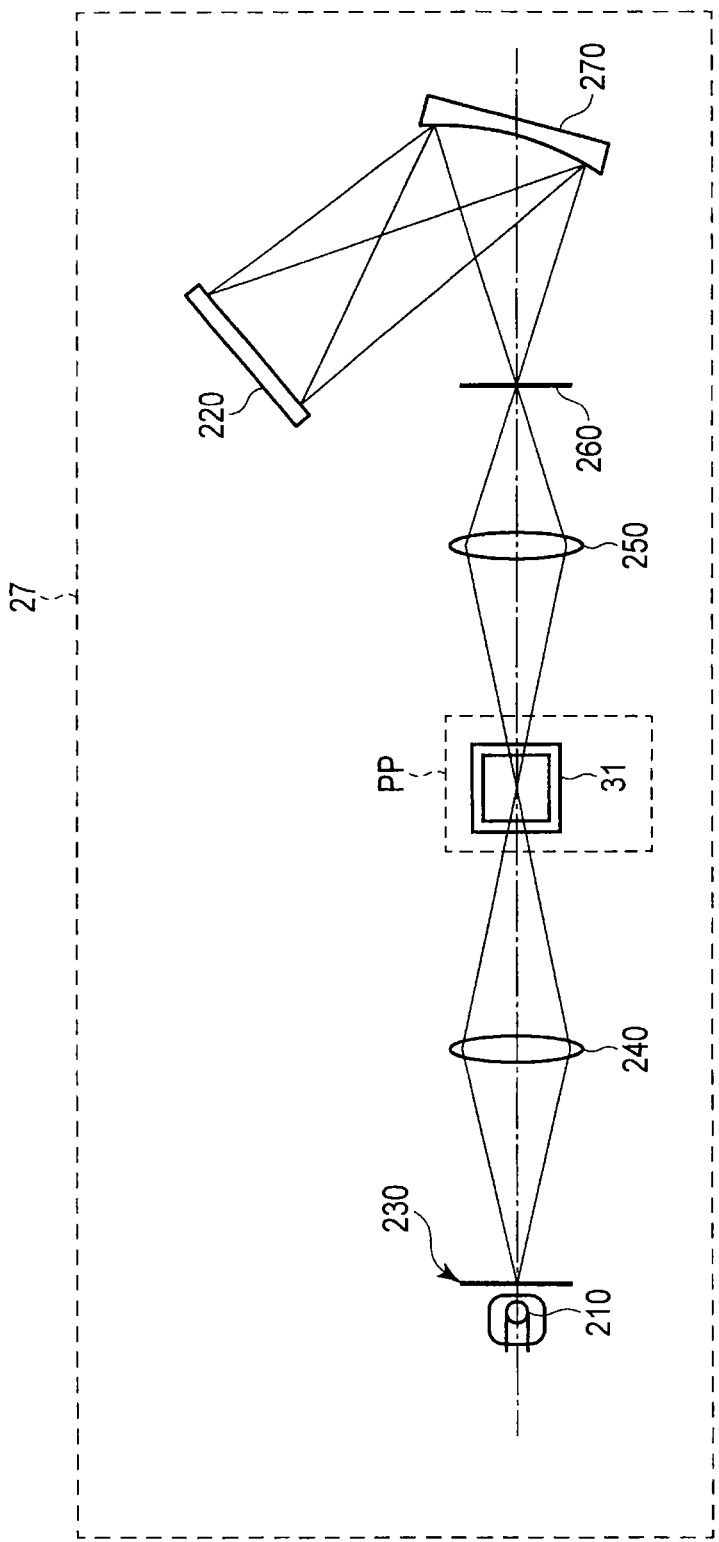
FIG. 4 is a view showing the detailed arrangement of a photometric mechanism shown in FIG. 1.

The photometric mechanism 27 according to this embodiment will be described next. FIG. 4 is a view showing the detailed arrangement of the photometric mechanism 27 according to this embodiment. As shown in FIG. 4, the photometric mechanism 27 includes a lamp such as a halogen lamp or a tungsten lamp as the photometric light source 210. The lamp 210 generates light. The reaction disk 11 receives a driving signal supplied from the analysis mechanism control unit 3, and sequentially passes the plurality of cuvettes 31 through the predetermined position (photometric position) PP in the optical system. A slit 230 and a lens 240 are provided in the optical path between the lamp 210 and the photometric position PP. The slit 230 limits the amount of light from the lamp 210. The lens 240 condenses the light from the slit 230. The light condensed by the lens 240 passes through the cuvette 31.

The light that has passed through the cuvette 31 and the reaction liquid in it at the photometric position PP is received by the photometric detector 220 via a lens 250, a slit 260, and a spectroscope 270. The lens 250 condenses the light that has passed through the cuvette 31 and the reaction liquid in it. The slit 260 limits the amount of light condensed by the lens 250. The spectroscope 270 spectrally disperses the light from the slit 260. As the spectroscope 270, for example, a diffraction grating is used. The diffraction grating is formed from, for example, a concave mirror having a plurality of grooves (grid lines) formed in the mirror surface at equal intervals. The light that has irradiated the diffraction grating is spatially dispersed by the grid lines on the diffraction grating for each wavelength. The photometric detector 220 receives the light spectrally dispersed by the spectroscope 270, and generates a photometric signal corresponding to the intensity of the received light. The photometric detector 220 includes, for example, a plurality of light-receiving elements one- or two-dimensionally arranged on a surface perpendicular to the optical path of the light from the spectroscope 270. Each light-receiving element receives a light beam belonging to a wavelength band according to its arrangement position, and generates an analog electrical signal, that is, photometric signal corresponding to the intensity of the received light beam. For example, the light-receiving element is implemented by a photodiode.

A disturbance in the time-varying waveform of an analog photometric signal from the photometric detector 220 caused by a fluctuation of magnetic separation will be described next. A fluctuation of magnetic separation indicates a state in which magnetic separation does not spatially evenly progress, that is, a state in which magnetic separation is spatially uneven. The fluctuation of magnetic separation occurs when flux densities are spatially unevenly distributed due to geometrical shifts, a decrease in the magnetic force, and the like of the magnets 41.

Figure 5:
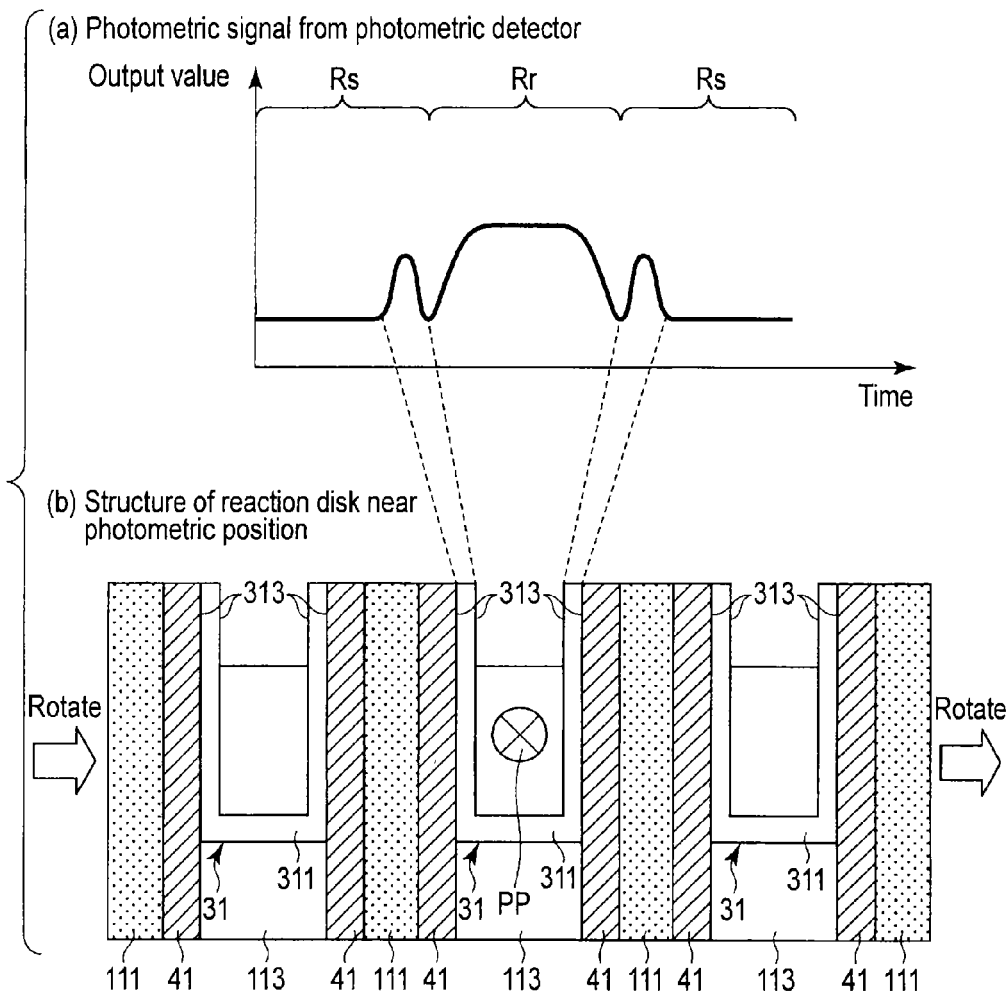
FIGS. 5(a) and 5(b) show views illustrating the typical time-varying waveform of a photometric signal from a photometric detector shown in FIG. 1 in association with normal inspection.

FIG. 5 shows views for explaining the typical time-varying waveform of a photometric signal in the cuvette 31 in association with normal inspection. In FIG. 5, (a) is a graph showing the typical time-varying waveform of a photometric signal in association with normal inspection. The ordinate of (a) in FIG. 5 represents the output value of the photometric signal, and the abscissa represents time. In FIG. 5, (b) is a view showing the structure of the reaction disk 11 near the photometric position PP. In this embodiment, normal inspection indicates inspection without magnetic separation. In a situation where the plurality of cuvettes 31 sequentially pass through the photometric position PP, the photometric mechanism 27 causes the photometric light source 210 to emit light toward the photometric position PP and causes the photometric detector 220 to detect the light. The time-varying waveform shown in (a) of FIG. 5 indicates the time-varying waveform concerning one cuvette 31. The time-varying waveform has a time range (to be referred to as a structural factor range hereinafter) Rs where the output value varies due to a structural factor such as the reaction disk 11 or the cuvette 31, and a time range (to be referred to as a reaction liquid factor range hereinafter) Rr where the output value varies due to the liquidity of the reaction liquid. In normal inspection, the sampling window is permanently preset to the reaction liquid factor range Rr.

As shown in (b) of FIG. 5, the reaction disk 11 holds the plurality of cuvettes 31 along the rotation direction. The magnets 41 are provided between the cuvettes 31. During rotation of the plurality of cuvettes 31 along the rotation direction, the photometric light source 210 of the photometric mechanism 27 irradiates the predetermined position (photometric position) PP of the rotation track of the cuvettes 31 with light. In normal inspection, the output value of the photometric signal in the reaction liquid factor range Rr becomes almost even, in other words, spatially almost even in accordance with the elapse of time, as shown in (a) of FIG. 5. The light sequentially irradiates a case 111, a thermostat 113, a wall portion 311 of a cuvette, the cuvette 31, the wall portion 311 of the cuvette, the thermostat 113, and the case 111.

FIG. 6 is a timing chart showing the time-varying waveform of a photometric signal according to the embodiment, that is, a typical time-varying waveform in a case where no fluctuation of magnetic separation occurs. As shown in FIG. 6, when magnetic separation is performed, the output value gradually increases from one end of the cuvette 31 to the center and gradually decreases from the center to the other end. In other words, when magnetic separation is performed, the time-varying waveform of the photometric signal in the reaction liquid factor range Rr has an extreme value. The extreme value is a value that should be used to calculate the measured value of a measurement item needing magnetic separation. When no fluctuation of magnetic separation occurs, the extreme value is located almost at the center of the reaction liquid factor range Rr.

FIG. 7 is a timing chart showing the time-varying waveform of a photometric signal according to the embodiment, that is, an example of a time-varying waveform in a case where a fluctuation of magnetic separation occurs. FIG. 8 is a timing chart showing the time-varying waveform of a photometric signal according to the embodiment, that is, another example of a time-varying waveform in a case where a fluctuation of magnetic separation occurs. As shown in FIGS. 7 and 8, when a fluctuation of magnetic separation occurs, the extreme value of the time-varying waveform of the photometric signal in the reaction liquid factor range Rr shifts from the center of the cuvette to the left side (temporally earlier than the center) or right side (temporally later than the center).

Even when magnetic separation is performed, as in normal inspection, when the sampling window is set to almost the entire reaction liquid factor range, values other than the extreme value are also used to calculate the measured value, and the reliability of the measured value degrades. Assume that the sampling window is set to only the center of the reaction liquid factor range so as not to use values other than the extreme value to calculate the measured value as much as possible. In this case, if a fluctuation of magnetic separation occurs, no extreme value may be generated in the sampling window. If no extreme value is generated in the sampling window, no accurate measured value can be obtained.

The signal processing unit 4 according to this embodiment sets the sampling window such that an accurate measured value can be calculated without any influence of the presence/absence of occurrence of a fluctuation of magnetic separation. More specifically, the signal processing unit 4 decides the sampling window in accordance with the spatial unevenness of magnetic separation by the magnets 41. In other words, the sampling window is corrected in accordance with the spatial unevenness of magnetic separation by the magnets 41. The sampling window is individually decided or corrected for each of the plurality of cuvettes 31.

FIG. 9 is a block diagram showing the arrangement of the signal processing unit 4 according this embodiment. As shown in FIG. 9, the signal processing unit 4 includes an extraction unit 470, an A/D converter 430, and a measurement range decision unit 450. The extraction unit 470 extracts the photometric signal within the reaction liquid factor range out of a photometric signal from the photometric detector 220 of the photometric mechanism 27. The photometric signal within the reaction liquid factor range can be extracted by a method using software, a method using hardware, or the like. Example 1 will be explained below.

The extraction unit 470 performs signal processing for the photometric signal from the photometric detector 220, and extracts the photometric signal within the reaction liquid factor range out of the photometric signal from the photometric detector 220. As the first extraction method, the extraction unit 470 stores the passage time of each cuvette 31 of the reaction disk 11 through the photometric position PP in advance, thereby measuring the times of the start point and end point of the reaction liquid factor range of each cuvette 31. The extraction unit 470 extracts the photometric signal from the start point to the end pint of the reaction liquid factor range, which are stored in advance, out of the photometric signal from the photometric detector 220.

The extraction unit 470 may extract the photometric signal by another method. For example, the extraction unit 470 may extract the photometric signal within the reaction liquid factor range out of the photometric signal from the photometric detector 220 by thinning processing, sampling processing, or the like.

Example 2 will be explained next.

FIG. 10 is a block diagram showing the arrangement of another signal processing unit 4'. As shown in FIG. 10, the signal processing unit 4' includes an extraction unit 410, the A/D converter 430, and the measurement range decision unit 450. The extraction unit 410 extracts the photometric signal within the reaction liquid factor range out of a photometric signal from the photometric detector 220 of the photometric mechanism 27 using a signal output from a detector 53 for cuvette of a cuvette detection mechanism (to be described later). The A/D converter 430 performs A/D conversion for the photometric signal from the extraction unit 410 and converts the analog photometric signal into a digital photometric signal. The measurement range decision unit 450 detects the extreme value of the time-varying waveform of the photometric signal from the A/D converter 430, and decides a predetermined time range including the detected extreme value as the sampling window.

FIG. 11 is a perspective view showing the outer appearance of a cuvette holder 115 and a cuvette detection mechanism 50 in the reaction disk 11 so as to explain the cuvette detection mechanism 50 according to this embodiment. The reaction disk 11 includes the plurality of cuvette holders 115 arranged almost circumferentially. FIG. 11 illustrates one cuvette holder 115. The cuvette holder 115 has a plurality of opening portions 117 capable of receiving the cuvettes 31. The cuvette 31 is inserted into each opening portion 117. A slit plate 119 is attached to the outer periphery of the cuvette holder 115. The slit plate 119 is provided with a plurality of blade-shaped members (to be simply referred to as blades hereinafter) 121. The blade 121 is formed from a member having a light blocking effect. A slit is formed between the adjacent blades 121. The slit plate 119 has a plurality of slits formed at positions corresponding to the plurality of cuvettes 31 (or opening portions 117). The slit plate 119 is attached to the cuvette holder 115 such that the plurality of blades 121 project to the outer side of the reaction disk 11.

The cuvette detection mechanism 50 configured to detect the cuvette 31 is provided near the photometric mechanism 27 in the case (not shown) of the automatic analyzer. The cuvette detection mechanism 50 includes a light source 51 and the detector 53. The light source 51 of the cuvette detection mechanism 50 will be referred to as a cuvette light source, and the detector 53 as a cuvette detector hereinafter. The cuvette light source 51 generates light. The cuvette detector 53 detects the light from the cuvette light source 51. An axis connecting the focal point of the cuvette light source 51 and the detection surface center of the cuvette detector 53 will be referred to as an optical axis A1. The cuvette light source 51 and the cuvette detector 53 are provided in the case of the automatic analyzer such that the optical axis A1 crosses the rotation track of the plurality of blades 121. The output signal from the cuvette detector 53 is supplied to the extraction unit 410. The output signal from the cuvette detector 53 will be referred to as a cuvette detection signal hereinafter.

Figure 12:
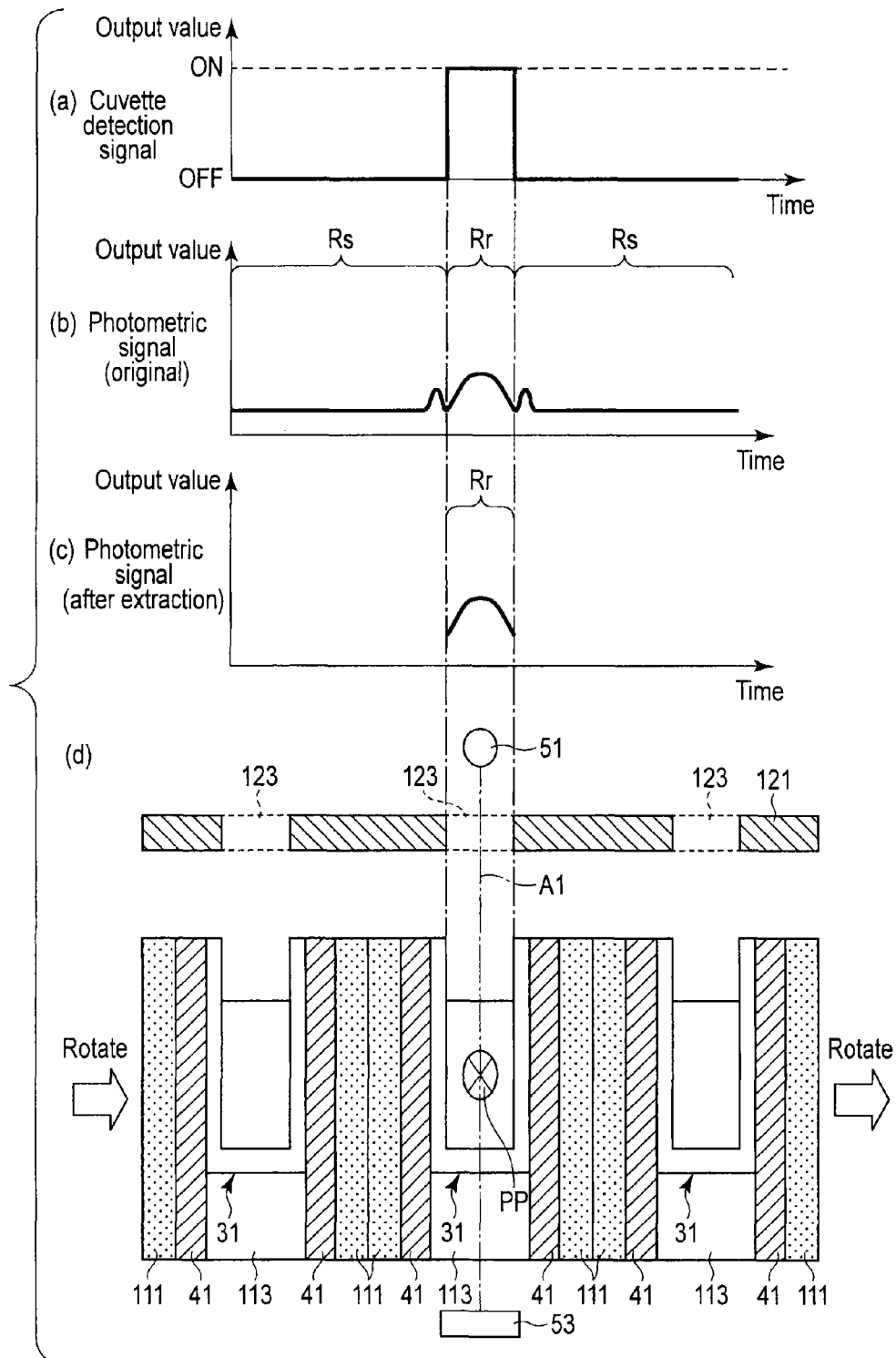
FIGS. 12(a)-12(d) show views illustrating the internal structure of the reaction disk near a photometric position and the relationship between the output value of a cuvette detection signal, the output value of a photometric signal (original), and the output value of a photometric signal (after extraction) according to Example 2 of the embodiment.

FIG. 12 shows views illustrating the internal structure of the reaction disk 11 near the photometric position PP and the relationship between the output value of the cuvette detection signal and the output value of the photometric signal. In FIG. 12, (a) is a timing chart showing the time-varying waveform of the output value of the cuvette detection signal. The ordinate of the graph of (a) in FIG. 12 represents the output value, and the abscissa represents time. In FIG. 12, (b) is a timing chart showing the time-varying waveform of the output value of a photometric signal (original). In FIG. 12, (c) is a timing chart showing the time-varying waveform of the output value of a photometric signal (after extraction). In FIG. 12, (d) is a plan view schematically showing the internal structure of the reaction disk 11 near the photometric position.

As shown in (d) of FIG. 12, the cuvette light source 51 and the cuvette detector 53 are provided on the reaction disk 11 such that the optical axis A1 becomes perpendicular to the photometric position PP. The plurality of blades 121 are positioned such that the optical axis A1 passes through a slit 123 when the interior of the cuvette 31 is passing through the photometric position PP. Hence, the cuvette detection signal is output as an OFF signal when the photometric position PP is passing through a portion other than the interior of the cuvette 31, and as an ON signal when the photometric position PP is passing through the interior of the cuvette 31. That is, during the period when the cuvette detection signal is the OFF signal, the photometric signal exists within the structural factor range Rs. During the period when the cuvette detection signal is the ON signal, the photometric signal exists within the reaction liquid factor range Rr. The cuvette detection signal is supplied to the extraction unit 410.

The extraction unit 410 receives the cuvette detection signal from the cuvette detector 53 and the photometric signal from the photometric detector 220. As shown in (c) of FIG. 12, during the period when the cuvette detection signal is the OFF signal, the extraction unit 410 does not extract the photometric signal from the photometric detector 220 and, for example, discards it. On the other hand, during the period when the cuvette detection signal is the ON signal, the extraction unit 410 extracts the photometric signal from the photometric detector 220. The extracted photometric signal is supplied to the A/D converter 430. The A/D converter 430 performs A/D conversion for the supplied photometric signal and converts it from an analog signal to a digital signal. The digital photometric signal is supplied to the measurement range decision unit 450.

As described above, when the extraction unit 470 or 410 extracts the photometric signal, the measurement range decision unit 450 performs sampling window decision processing.

Figure 15:
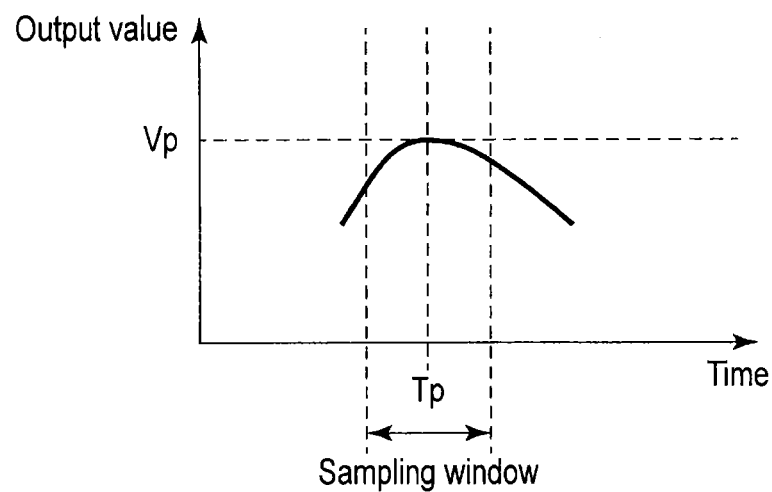
FIG. 15 is a timing chart showing the time-varying waveform of another photometric signal from the A/D converter in a case where a fluctuation of magnetic separation occurs so as to explain sampling window decision processing by the measurement range decision unit shown in FIG. 10.

FIG. 13 is a timing chart showing the time-varying waveform of a photometric signal from the A/D converter 430 in a case where no fluctuation of magnetic separation occurs so as to explain sampling window decision processing by the measurement range decision unit 450. FIG. 14 is a timing chart showing the time-varying waveform of a photometric signal from the A/D converter 430 in a case where a fluctuation of magnetic separation occurs so as to explain sampling window decision processing by the measurement range decision unit 450. FIG. 15 is a timing chart showing the time-varying waveform of another photometric signal from the A/D converter 430 in a case where a fluctuation of magnetic separation occurs so as to explain sampling window decision processing by the measurement range decision unit 450.

As shown in FIGS. 13, 14, and 15, the measurement range decision unit 450 analyzes the time-varying waveform of the photometric signal supplied from the A/D converter 430, and detects an extreme value Vp. Extreme value detection is done by a known method such as differential analysis of the time-varying waveform of the photometric signal. Upon detecting the extreme value Vp, the measurement range decision unit 450 specifies a time Tp at which the photometric signal obtains the extreme value Vp, and sets a predetermined time range including the time Tp to the sampling window. Even when the extreme value is not located at the center of the cuvette 31, the predetermined time range is set to improve the measurement accuracy. The predetermined time range is set in correspondence with, for example, two or three sampling points in each of the forward and backward directions from the extreme value Vp. The predetermined time range can be set to an arbitrary value by the user via an input unit or the like. Data associated with the sampling window is supplied to the measurement item calculation unit 5.

Note that in normal inspection, the measurement range decision unit 450 equally sets the sampling window to the ON signal output time range, that is, the reaction liquid factor range.

As described above, the signal processing unit 4 can determine the spatial unevenness of magnetic separation by the magnets 41 in accordance with the extreme value appearance timing within the reaction liquid factor range and decide or correct the time range of the photometric signal in accordance with the spatial unevenness of magnetic separation.

After that, the measurement item calculation unit 5 calculates the average value of the output values of photometric signals in the sampling window for each of the plurality of cuvettes 31, and individually calculates the measured value of the measurement item based on the average value. Each cuvette 31 storing the reaction liquid to be measured is optically measured a plurality of times by the photometric mechanism 27. Every time a photometric signal and data associated with the sampling window are supplied from the signal processing unit 4, the measurement item calculation unit 5 calculates the average value of the output values of photometric signals in the sampling window. The measured value is displayed by the display unit 7.

A description of sampling window decision processing according to this embodiment will be ended.

(Modification)

In the above embodiment, the automatic analyzer decides the time range of the photometric signal as a use range to be used to measure a measurement item. However, the embodiment is not limited to this. An automatic analyzer according to a modification decides a spatial range of a photometric signal as a use range to be used to measure a measurement item. The automatic analyzer 1 according to the modification will be described below. Note that the same reference numerals as in the embodiment denote constituent elements having almost the same functions in the following explanation, and a repetitive description thereof will be made only when necessary.

Figure 16:
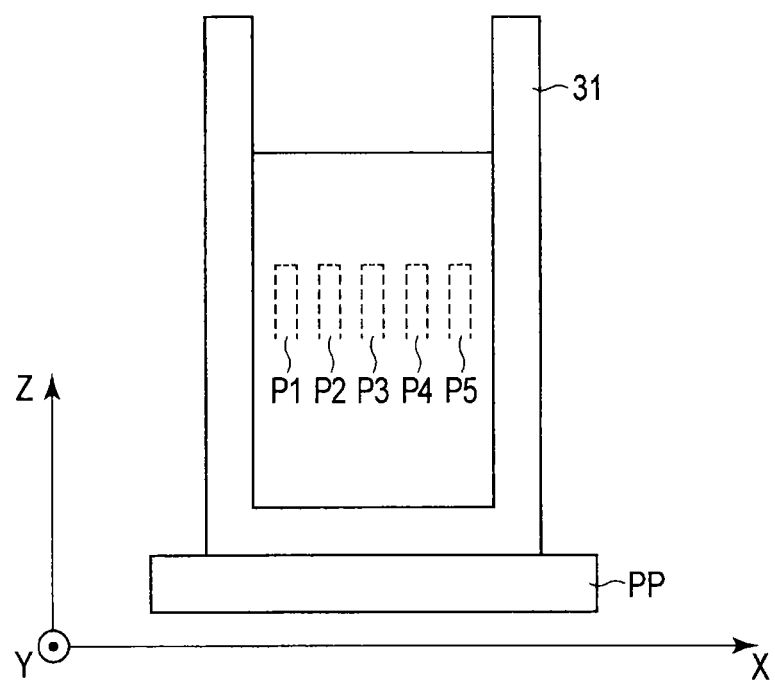
FIG. 16 is a view for schematically explaining an example of light irradiation on a cuvette by a photometric mechanism according to a modification.

FIG. 16 is a view for schematically explaining an example of light irradiation on the cuvette 31 by a photometric mechanism according to the modification. Note that the automatic analyzer according to the modification includes no cuvette holding mechanism like the reaction disk 11 configured to automatically pass the cuvette 31 through the photometric position PP.

As shown in FIG. 16, the cuvette 31 is arranged at the photometric position PP. For example, the height direction of the cuvette 31 will be referred to as a Z direction, the horizontal direction of the cuvette 31 as an X direction, and a direction perpendicular to the X and Z directions as a Y direction. The magnets 41 are arranged so as to face each other in the X direction with the cuvette 31 between them. That is, the X direction almost matches the direction of magnetic field application by the magnets 41. The Y direction almost matches the passage direction of light generated by the photometric mechanism. The cuvette 31 is arranged at the photometric position PP by, for example, the user. The photometric mechanism according to the modification is configured to be able to irradiate a plurality of regions Pn (n is an integer) in the cuvette 31 whose positions (to be referred to as X positions hereinafter) concerning the X direction are different from each other. The regions Pn in the cuvette 31 will be referred to as irradiation regions Pn hereinafter. For example, the set of the photometric light source 210 and the photometric detector 220 is provided for each irradiation region Pn. Note that if the single photometric light source 210 can irradiate the plurality of irradiation regions Pn with light, and the single photometric detector 220 can distinguishably detect a plurality of light components that have passed through the plurality of irradiation regions Pn, only one set of the photometric light source 210 and the photometric detector 220 may be provided for the plurality of irradiation regions Pn. The number of irradiation regions Pn can be set to an arbitrary number of 2 or more.

To measure a variation in the output values of photometric signals concerning the X direction, one of the plurality of irradiation regions Pn is set almost at the center concerning the X direction, and two of the plurality of irradiation regions Pn are set almost at two ends concerning the X direction. For example, as shown in FIG. 16, five irradiation regions are set concerning the X positions. The photometric mechanism according to the modification parallelly irradiates the plurality of irradiation regions Pn with light, detects light components that have passed through the plurality of irradiation regions Pn, and outputs a plurality of photometric signals Sn corresponding to the plurality of irradiation regions Pn, respectively.

Figure 17:
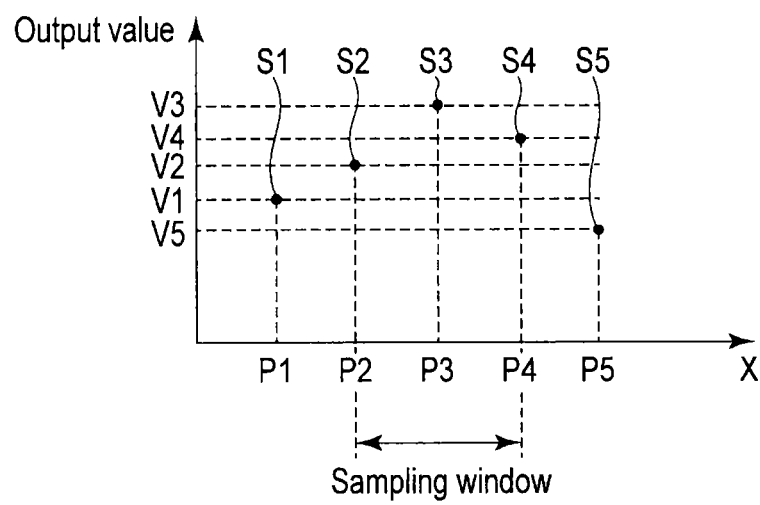
FIG. 17 is a graph showing the output values of a plurality of photometric signals respectively corresponding to a plurality of irradiation regions in a case where no fluctuation of magnetic separation occurs.

Photometric signal use range decision processing by the signal processing unit 4 according to the modification will be described next. FIG. 17 is a graph showing the output values of the plurality of photometric signals Sn respectively corresponding to the plurality of irradiation regions Pn in a case where no fluctuation of magnetic separation occurs.

Figure 18:
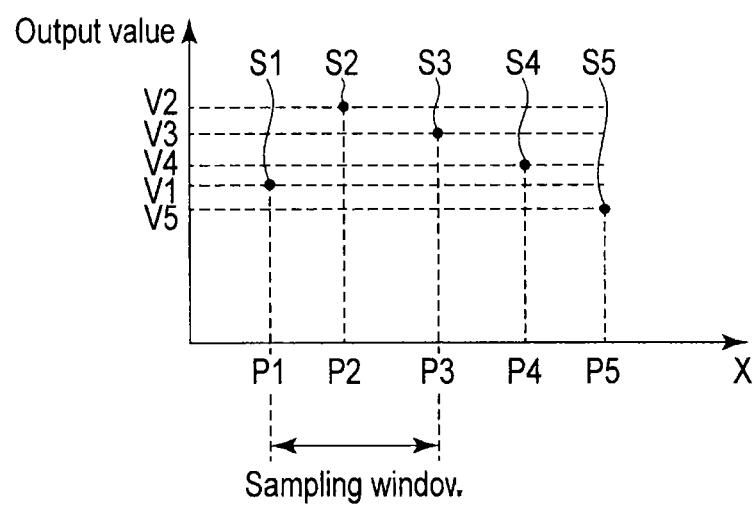
FIG. 18 is a graph showing the output values of a plurality of photometric signals Sn respectively corresponding to a plurality of irradiation regions Pn in a case where a fluctuation of magnetic separation occurs.

FIG. 18 is a graph showing the output values of the plurality of photometric signals Sn respectively corresponding to the plurality of irradiation regions Pn in a case where a fluctuation of magnetic separation occurs. FIG. 19 is another graph showing the output values of the plurality of photometric signals Sn respectively corresponding to the plurality of irradiation regions Pn in a case where a fluctuation of magnetic separation occurs. Note that the irradiation regions in FIGS. 17, 18, and 19 are set at five positions in correspondence with FIG. 16. A photometric signal S1 derives from light that irradiates an irradiation region P1. A photometric signal S2 derives from light that irradiates an irradiation region P2. A photometric signal S3 derives from light that irradiates an irradiation region P3. A photometric signal S4 derives from light that irradiates an irradiation region P4. A photometric signal S5 derives from light that irradiates an irradiation region P5.

As shown in FIG. 17, when no fluctuation of magnetic separation occurs, magnetic separation spatially evenly progresses. Hence, out of the plurality of photometric signals S1, S2, S3, S4, and S5 concerning the X direction, an output value V3 of the photometric signal S3 almost at the center concerning the X direction has the extreme value. On the other hand, as shown in FIGS. 18 and 19, when a fluctuation of magnetic separation occurs, magnetic separation spatially unevenly progresses. Hence, out of the plurality of photometric signals concerning the X direction, the output value of a photometric signal other than that almost at the center concerning the X direction has the extreme value. For example, as shown in FIG. 18, an output value V2 of the photometric signal S2 on the left side of the center concerning the X direction has the extreme value. Alternatively, as shown in FIG. 19, an output value V4 of the photometric signal S4 on the right side of the center concerning the X direction has the extreme value. That is, the X position, from the center, of the irradiation region Pn corresponding to the photometric signal Sn having the extreme value varies in accordance with the spatial unevenness of magnetic separation.

The signal processing unit 4 monitors the output values of the plurality of photometric signals S1, S2, S3, S4, and S5 concerning the X direction, and detects the extreme value. The signal processing unit 4 decides the range, that is, the output signal to be used to measure a measurement item in accordance with the position of the irradiation region Pn corresponding to the photometric signal having the detected extreme value. More specifically, the signal processing unit 4 sets a predetermined spatial range including the irradiation region Pn corresponding to the photometric signal having the detected extreme value. The predetermined spatial range is a spatial range corresponding to a predetermined number of irradiation regions including, almost at the center, the irradiation region Pn corresponding to the photometric signal Sn having the detected extreme value. The predetermined spatial range is limited to a range narrower than all the irradiation regions Pn. For example, the predetermined spatial range is defined as a range including three irradiation regions including, almost at the center, the irradiation region Pn corresponding to the photometric signal Sn having the detected extreme value. The signal processing unit 4 sets the sampling window to output signals corresponding to the irradiation regions included in the predetermined spatial range. For example, when the photometric signal S3 has the extreme value, as shown in FIG. 17, the sampling window is set to the photometric signals S2, S3, and S4 corresponding to the irradiation regions P2, P3, and P4, respectively. When the photometric signal S2 has the extreme value, as shown in FIG. 18, the sampling window is set to the photometric signals S1, S2, and S3 corresponding to the irradiation regions P1, P2, and P3, respectively. When the photometric signal S4 has the extreme value, as shown in FIG. 19, the sampling window is set to the photometric signals S3, S4, and S5 corresponding to the irradiation regions P3, P4, and P5, respectively.

As described above, the signal processing unit 4 can determine the spatial unevenness of magnetic separation by the magnets 41 in accordance with the extreme value appearance position among the plurality of irradiation regions and decide or correct the spatial range of the photometric signal in accordance with the spatial unevenness of magnetic separation.

A description of sampling window decision processing according to the modification will be ended.

When the sampling window is set, the measurement item calculation unit 5 calculates the measured value of the measurement item based on the photometric signal in the sampling window, as in the above-described embodiment.

(General Remarks)

As described above, the automatic analyzer 1 according to the embodiment includes the magnetic field generators 41, the photometric mechanism 27, the signal processing unit 4, and the measurement item calculation unit 5. The magnetic field generators 41 cause magnetic separation in the reaction liquid stored in the cuvette 31 by magnetic particles. The photometric mechanism 27 includes the photometric light source 210 configured to generate light, and the photometric detector 220 configured to detect the light generated by the photometric light source 210 and passed through the reaction liquid stored in the cuvette 31 and generate a photometric signal corresponding to the detected light. The measurement item calculation unit 5 measures a measurement item based on the output signal from the photometric detector 220. The signal processing unit 4 decides the use range of the photometric signal to be used to measure a measurement item in accordance with the spatial unevenness of magnetic separation by the magnetic field generators 41.

With the above-described arrangement, in inspection with magnetic separation, the automatic analyzer 1 decides the use range of the photometric signal in accordance with the spatial unevenness of magnetic separation by the magnetic field generators 41. In other words, the automatic analyzer 1 corrects the use range of the photometric signal in accordance with the spatial unevenness of magnetic separation by the magnetic field generators 41. With this processing, the automatic analyzer 1 can individually set a robust sampling window without any influence of the presence/absence of occurrence of a fluctuation of magnetic separation for each cuvette 31. Accordingly, the measured value of a measurement item is always accurate without any influence of the presence/absence of occurrence of a fluctuation of magnetic separation in the cuvette 31. Hence, the user can rely on the measured value of the measurement item.

Note that in the above description, the measurement range decision unit 450 detects, as the extreme value, the maximum value of the time-varying waveform of a photometric signal or a plurality of photometric signals respectively corresponding to a plurality of irradiation regions in the X direction. However, the embodiment is not limited to this. For example, the measurement range decision unit 450 may detect, as the extreme value, the minimum value of the time-varying waveform of a photometric signal or a plurality of photometric signals respectively corresponding to a plurality of irradiation regions in the X direction. This makes it possible to set an optimum sampling window according to the liquidity, measurement item, or the like.

Application examples of the automatic analyzer 1 according to this embodiment will be described next. Note that the following application examples are applicable to both an embodiment in which a time range is decided as a use range as in this embodiment and an embodiment in which a spatial range is decided as a use range as in the modification. However, for the sake of descriptive simplicity, the following application examples will be explained based on an embodiment in which a time range is decided as a use range as in this embodiment.

Application Example 1

A situation in which a fluctuation of magnetic separation occurs is not preferable. The determination unit 6 of the automatic analyzer 1 determines based on a photometric signal whether a fluctuation of magnetic separation has occurred.

Figure 21:
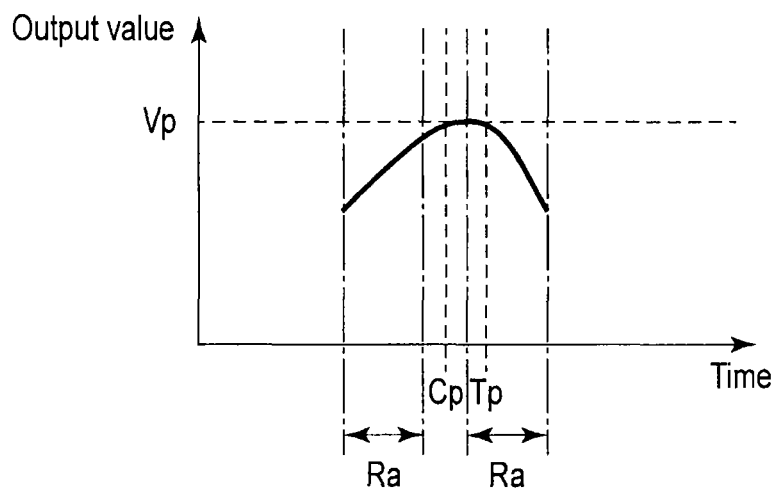
FIG. 21 is a timing chart showing the time-varying waveform of a photometric signal from the A/D converter in a case where a fluctuation of magnetic separation occurs so as to explain determination processing of the determination unit shown in FIG. 1.
Figure 22:
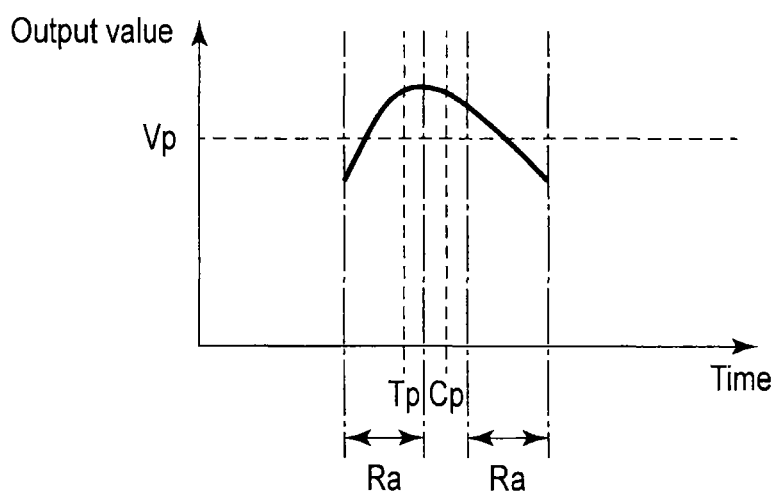
FIG. 22 is a timing chart showing the time-varying waveform of another photometric signal from the A/D converter in a case where a fluctuation of magnetic separation occurs so as to explain determination processing of the determination unit shown in FIG. 1.

FIG. 20 is a timing chart showing the time-varying waveform of a photometric signal from the A/D converter 430 in a case where no fluctuation of magnetic separation occurs so as to explain determination processing of the determination unit 6. FIG. 21 is a timing chart showing the time-varying waveform of a photometric signal from the A/D converter 430 in a case where a fluctuation of magnetic separation occurs so as to explain determination processing of the determination unit 6. FIG. 22 is a timing chart showing the time-varying waveform of another photometric signal from the A/D converter 430 in a case where a fluctuation of magnetic separation occurs so as to explain determination processing of the determination unit 6.

As shown in FIGS. 20, 21, and 22, the determination unit 6 determines whether the extreme value is included in a predetermined time range (to be referred to as a determination time range hereinafter) Ra out of the time-varying waveform of a photometric signal from the signal processing unit 4 or 4'. The determination time range Ra is set to a time range where a peak is assumed to be generated when a fluctuation of magnetic separation occurs or a time range where a peak is assumed not to be generated when no fluctuation of magnetic separation occurs. The determination time range can arbitrarily be set by the user via the operation unit 8. The determination unit 6 determines whether the time-varying waveform of the photometric signal has the extreme value Vp in the determination time range. For example, in FIG. 20, the extreme value Vp does not exist in the determination time range. In this case, the determination unit 6 generates a signal (to be referred to as a non-warning signal hereinafter) representing that no extreme value exists in the determination time range Ra. In FIGS. 21 and 22, the extreme value Vp exists in the determination time range Ra. In these cases, the determination unit 6 generates a signal (to be referred to as a warning signal hereinafter) representing that the extreme value exists in the determination time range Ra. The non-warning signal and the warning signal are supplied to the system control unit 10. Upon receiving the non-warning signal, the system control unit 10 notifies that no fluctuation of magnetic separation exists. Upon receiving the warning signal, the system control unit 10 notifies that a fluctuation of magnetic separation exists. As the notification means, for example, display by the display unit 7 is used. For example, when the non-warning signal is supplied to the system control unit 10, the display unit 7 displays a message or mark representing that no fluctuation of magnetic separation exists. When the warning signal is supplied to the system control unit 10, the display unit 7 displays a message or mark representing that a fluctuation of magnetic separation exists. The message or mark representing the presence/absence of a fluctuation of magnetic separation is displayed beside the measured value of a measurement item. Note that other than display by the display unit 7, a sound from a loudspeaker or lighting of a lamp may be used as the notification means.

As described above, according to Application Example 1, it is possible to notify the presence/absence of occurrence of a fluctuation of magnetic separation. Hence, the user can know the presence/absence of a fluctuation of magnetic separation. The user can thus know whether the measured value of a measurement item includes a fluctuation of magnetic separation, and the reliability of the measured value further improves. The user who knows that a fluctuation of magnetic separation has occurred can tackle a pursuit of the cause of the fluctuation of magnetic separation.

Application Example 2

The system control unit 10 sets a measurement item for each of the plurality of cuvettes 31. For example, the system control unit 10 switches the photometric method between an item that requires magnetic separation and an item that does not require magnetic separation.

For a photometric signal concerning a measurement item that requires magnetic separation, the measurement range decision unit 450 decides the sampling window to a predetermined time range including the extreme value in accordance with the time-varying waveform of the photometric signal, as described above. For a photometric signal concerning a measurement item that does not require magnetic separation, the measurement range decision unit 450 decides the sampling window to the entire reaction liquid factor range or a predetermined time range. The measurement item calculation unit 5 calculates the average value of the output values of photometric signals in the sampling window for each of the measurement item requiring magnetic separation and the measurement item of normal inspection, and calculates the measured value of each measurement item based on the calculated average value. The measured value of each measurement item is displayed by the display unit 7.

According to Application Example 2, it is possible to set an optimum sampling window for each of a measurement item that requires magnetic separation and a measurement item of normal inspection that does not require magnetic separation. It is therefore possible to calculate a measured value of the best accuracy for each of the measurement item that requires magnetic separation and the measurement item of normal inspection.

According to this embodiment, the reliability of a measurement result can thus improve in the automatic analyzer including the magnetic field generators configured to apply magnetic fields to the cuvettes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An automatic analyzer comprising:
   a magnetic field generator configured to cause magnetic separation in a reaction liquid stored in a cuvette by magnetic particles;
   a photometric unit including a light source configured to generate light, and a detector configured to detect the light generated by the light source and passed through the reaction liquid stored in the cuvette, and to generate an output signal corresponding to the detected light;
   a cuvette holding mechanism configured to hold a plurality of cuvettes;
   a driving mechanism configured to drive the cuvette holding mechanism so that the plurality of cuvettes sequentially pass through a photometric position; and
   circuitry configured to
      decide a use range of the output signal to be used to measure a measurement item in accordance with a time-variation of the output value of the output signal, and
      measure the measurement item based on the use range of the output signal, wherein
   the circuitry detects an extreme value of the time-variation of the output value of the output signal, specifies a time at which the output signal obtains the extreme value, and sets the use range to a predetermined time duration that includes the specified time, and
   the magnetic field generator is provided to sandwich each of the plurality of cuvettes to apply a magnetic field in a direction in which each of the plurality of cuvettes passes through the photometric position.

2. The apparatus according to claim 1, wherein
   the detector repetitively generates an output signal corresponding to light that has passed through the reaction liquid stored in the cuvette, and
   the circuitry is further configured to decide, as a use range of the repetitively generated output signal, a time range to be used to measure the measurement item out of the repetitively generated output signal in accordance with a time-variation of an output value of the repetitively generated output signal.

3. The apparatus according to claim 2, wherein
   the circuitry individually decides a corresponding use range for each of the plurality of cuvettes in accordance with a time-varying waveform of the repetitively generated output signal.

4. The apparatus according to claim 1, wherein the magnetic field generator is provided in the cuvette holding mechanism to apply a magnetic field to each of the plurality of cuvettes.

5. The apparatus according to clan 3, wherein the circuitry is further configured to
   determine a presence of a fluctuation of the magnetic separation in each of the plurality of cuvettes based on the time-varying waveform of the repetitively generated output signal to generate a determination result, and
   a signal the determination result.

6. The apparatus according to claim 5, wherein the circuitry signals the determination result together with a measured value of the measurement item.

7. The apparatus according to claim 5, wherein the circuitry determines the presence of the fluctuation of the magnetic separation based on a time at which an extreme value of the time-varying waveform of the repetitively generated output signal is detected.

8. The apparatus according to claim 2, wherein the circuitry detects an extreme value of a time-varying waveform of the repetitively generated output signal, and sets the use range of the repetitively generated output signal to be the predetermined time duration that includes the extreme value.

9. The apparatus according to claim 8, wherein the extreme value is a maximum value.

10. The apparatus according to claim 8, wherein the extreme value is a minimum value.

11. The apparatus according to claim 1, wherein the circuitry is further configured to
    set necessity of the magnetic separation for each of a plurality of emetics, and
    set a corresponding use range of a corresponding output signal in accordance with a time-variation of an output value of the corresponding output signal for a cuvette set to require the magnetic separation, wherein the corresponding use range is a preset range for a cuvette set to not require the magnetic separation.

12. The apparatus according to claim 1, wherein
    the light source irradiates a plurality of regions whose positions in the cuvette are different from each other with the light,
    the detector generates a plurality of output signals corresponding to the light that has passed through the plurality of regions, and
    the circuitry decides a respective output signal to be used to measure the measurement item out of the plurality of output signals in accordance with a position of an output value of the respective output signal, and decides a corresponding use range based on the decided respective output.

13. The apparatus according to claim 12, wherein the circuitry detects a substantially temporally matching extreme value in the plurality of output signals, and decides an output signal corresponding to at least one region near the extreme value out of the plurality of regions.

14. The apparatus according to claim 13, wherein the extreme value is a maximum value.

15. The apparatus according to claim 13, wherein the extreme value is a minimum value.

16. The apparatus according to claim 1, wherein the magnetic field generator includes a pair of magnetic field generators, and the pair of magnetic field generators are arranged so as to face a direction perpendicular to a traveling direction of the light generated by the light source.

17. The apparatus according to claim 1, wherein the circuitry is further configured to switch the use range depending on whether the measurement item requires the magnetic separation.

18. An automatic analyzer comprising:
    a magnetic field generator configured to cause magnetic separation in a reaction liquid stored in a cuvette by magnetic particles;
    a photometric unit including a light source configured to generate light, and a detector configured to detect the light generated by the light source and passed through the reaction liquid stored in the cuvette, and to generate an output signal corresponding to the detected light;
    a cuvette holding mechanism configured to hold a plurality of cuvettes;
    a driving mechanism configured to drive the cuvette holding mechanism so that the plurality of cuvettes sequentially pass through a photometric position; and
    circuitry configured to correct a range of the output signal in accordance with a time-variation of the output value of the output signal; and measure a measurement item based on the range of the output signal, wherein the circuitry detects an extreme value of the time-variation of the output value of the output signal, specifies a time at which the output signal obtains the extreme value, and correct the range by setting the range to a predetermined time duration that includes the specified time, and the magnetic field generator is provided to sandwich each of the plurality of cuvettes to apply a magnetic field in a direction in which each of the plurality of cuvettes passes through the photometric position.

* * * * *